(12) United States Patent
Schaffer

(10) Patent No.: US 10,315,012 B2
(45) Date of Patent: Jun. 11, 2019

(54) TITANIUM-NIOBIUM-HAFNIUM ALLOY SHAPE MEMORY WIRE

(71) Applicant: FORT WAYNE METALS RESEARCH PRODUCTS CORPORATION, Fort Wayne, IN (US)

(72) Inventor: Jeremy E. Schaffer, Leo, IN (US)

(73) Assignee: FORT WAYNE METALS RESEARCH PRODUCTS CORP, Fort Wayne, IN (US)

( * ) Notice: Subject to any disclaimer, the term of this patent is extended or adjusted under 35 U.S.C. 154(b) by 530 days.

(21) Appl. No.: 14/889,101

(22) PCT Filed: May 6, 2014

(86) PCT No.: PCT/US2014/036961
§ 371 (c)(1),
(2) Date: Nov. 4, 2015

(87) PCT Pub. No.: WO2014/182691
PCT Pub. Date: Nov. 13, 2014

(65) Prior Publication Data
US 2016/0151610 A1    Jun. 2, 2016

Related U.S. Application Data

(60) Provisional application No. 61/819,798, filed on May 6, 2013.

(51) Int. Cl.
*A61L 31/02* (2006.01)
*A61L 31/14* (2006.01)
(Continued)

(52) U.S. Cl.
CPC ........... *A61M 25/09* (2013.01); *A61F 2/86* (2013.01); *A61L 31/022* (2013.01); *A61L 31/14* (2013.01);
(Continued)

(58) Field of Classification Search
CPC ........ A61F 2230/008; A61F 2230/0093; A61F 2002/016; A61F 2/013; A61F 2/86;
(Continued)

(56) References Cited

U.S. PATENT DOCUMENTS

| 7,128,757 B2 * | 10/2006 | Boylan | A61F 2/915 623/1.18 |
| 2003/0069492 A1 * | 4/2003 | Abrams | A61L 31/022 600/407 |

(Continued)

OTHER PUBLICATIONS

International Search Report and Written Opinion dated Dec. 1, 2014 of International Application No. PCT/US22014/036961.
(Continued)

*Primary Examiner* — Jacob J Cigna
*Assistant Examiner* — Lee A Holly
(74) *Attorney, Agent, or Firm* — Faegre Baker Daniels LLP

(57) ABSTRACT

Ti—Nb—Hf/Zr—(Cr) alloy shape-memory wires are provided which are suitable for use in medical devices and actuators, and methods for manufacturing such wires are provided. The present shape-memory Ti—Nb—Hf/Zr—(Cr) alloy is a superelastic wire material particularly suited for in vivo applications. For example, the present Ti—Nb—Hf/Zr—(Cr) alloy wire is radiopaque, thereby enabling surgical use of a monolithic, shape-memory alloy wire while preserving the ability to monitor the in vivo location of the wire through X-ray or other radiation-based imaging systems. In addition, the present Ti—Nb—Hf/Zr—(Cr) alloy can be manufactured to exhibit shape-memory alloy material prop-
(Continued)

erties without the use of nickel as an alloy constituent, thereby accommodating nickel-sensitive patients. The present Ti—Nb—Hf/Zr—(Cr) alloy can also be processed to exhibit a martensite/austenite transformation temperature near body-temperature, i.e., 37° C., so that shape-memory effects can be utilized to accomplish work in vivo.

23 Claims, 11 Drawing Sheets

(51) Int. Cl.
| | |
|---|---|
| C22C 14/00 | (2006.01) |
| C22C 30/00 | (2006.01) |
| A61M 25/09 | (2006.01) |
| C21D 8/06 | (2006.01) |
| A61F 2/86 | (2013.01) |
| C21D 1/26 | (2006.01) |
| C21D 9/52 | (2006.01) |
| C22F 1/00 | (2006.01) |
| C22F 1/18 | (2006.01) |

(52) U.S. Cl.
CPC ............... *C21D 1/26* (2013.01); *C21D 8/06* (2013.01); *C21D 9/525* (2013.01); *C22C 14/00* (2013.01); *C22C 30/00* (2013.01); *C22F 1/006* (2013.01); *C22F 1/183* (2013.01); *A61F 2210/0014* (2013.01); *A61L 2400/16* (2013.01); *A61M 2025/09141* (2013.01); *C21D 2201/01* (2013.01)

(58) Field of Classification Search
CPC ... A61F 2210/0014; A61M 2025/0002; A61M 25/09; A61M 2025/09141; C22F 1/183; C22F 1/006; C21D 9/525; C21D 1/26; C21D 8/06; C21D 2201/01; A21D 2201/01; A61L 31/022; A61L 31/14; A61L 2400/16; C22C 30/00; C22C 14/00
See application file for complete search history.

(56) References Cited

U.S. PATENT DOCUMENTS

| | | | |
|---|---|---|---|
| 2007/0137742 A1* | 6/2007 | Hao | ................. C22C 14/00 148/671 |
| 2008/0195194 A1* | 8/2008 | Pacetti | ................. A61L 27/06 623/1.16 |
| 2010/0043199 A1 | 2/2010 | Rice et al. | |
| 2012/0046575 A1* | 2/2012 | Brown | ................. A61M 25/09 600/585 |

OTHER PUBLICATIONS

Gonzalez et al., "Design and Characterization of New Ti—Nb—Hf Alloys", Journal of Materials Engineering and Performance, vol. 18(5-6) Aug. 2009, pp. 490-495.
Gonzalez et al., "Optimization of the Ti—16.2Hf—24Nb—1Zr Alloy by Cold Working", Journal of Materials Engineering and Performance, vol. 18(5-6) Aug. 2009, pp. 506-510.
Herranz et al., "Microstructural Characterization of a Potential Superelastic Nickel-Free Titanium Alloy", Microscopy oat the Frontiers of Science 2013, Terragona, Spain.
Baker, "The Shape-Memory Effect in a Titanium-35 wt.-% Niobium Alloy", Metal Science Journal, 1971, vol. 5.
Kim et al., "Martensitic transformation, shape memory effect and superelasticity of Ti—Nb binary alloys", Acta Materialia 54 (2006), pp. 2419-2429.
Kim et al., "Shape Memory Behavior of Ti—22Nb—(0.5-2.0)O(at%) Biomedical Alloys", Materials Transactions, vol. 46, No. 4 (2005) pp. 852-857.
Kim et al., "Mechanical Properties and Shape Memory Behavior of Ti—Nb Alloys", Materials Transactions, vol. 45, No. 7 (2004) pp. 2443-2448.

* cited by examiner

TITANIUM-NIOBIUM-HAFNIUM ALLOY SHAPE MEMORY WIRE

CROSS-REFERENCE TO RELATED APPLICATIONS

The present application is a national-stage filing of International Patent Application No. PCT/US2014/036961, which claims the benefit under Title 35, U.S.C. § 119(e) of U.S. Provisional Patent Application Ser. No. 61/819,798 filed May 6, 2013, both of which are entitled "TITANIUM-NIOBIUM-HAFNIUM ALLOY SHAPE MEMORY WIRE," the entire disclosures of which are hereby expressly incorporated by reference herein.

BACKGROUND

1. Technical Field of the Disclosure

The present disclosure relates to shape-memory alloy wire and, in particular, relates to a method of manufacturing wire made of a shape memory alloy which demonstrates wire properties appropriate for in vivo use, as well as medical devices made with such wire.

2. Description of the Related Art

Shape memory materials are materials that "remember" their original shape, and which, after being deformed, return to that shape either spontaneously or by applying heat to raise their temperature above a processing and material related threshold known as the transformation temperature. Materials which are heated to recover shape are commonly referred to in the art as "shape memory" materials, whereas materials which spontaneously recover to a particular shape upon removal of a constraining force are commonly referred to as pseudoelastic materials. Shape memory materials, possessing relatively high transformation temperatures, are commonly used in thermally activated actuation devices, for example in military, automotive or robotic devices whereas pseudoelastic materials are commonly used in highly flexible implantable medical devices.

Pseudoelasticity, sometimes called superelasticity, is a reversible response to an applied stress, caused by a phase transformation between the austenite or parent phase and the martensite or daughter phase of a crystal. FIG. 1 schematically illustrates superelastic behavior in the context of a stress-strain curve for a superelastic material. As illustrated, a superelastic stress-strain curve exhibits a nonlinear correlation between load (i.e., stress) and displacement (i.e., strain). During initial loading across a first change in strain $\Delta\varepsilon_1$, stress and strain are linearly correlated, that is, the material exhibits linear elastic behavior. Superelastic behavior is exhibited by the shape of the stress-strain curve across $\Delta\varepsilon_2$, which disrupts the end of this linear elastic correlation with a substantial increase in strain with little or no increase in stress. The magnitude of $\Delta\varepsilon_2$ can be considered to be the "amount" or level of loading superelasticity exhibited by a material. During this period, phase transformation occurs between austenite and martensite. At the end of the phase transformation, the material may experience a further linear elastic deformation through $\Delta\varepsilon_3$. Upon unloading, linear elastic behavior is again exhibited for the initial unloading process, with superelastic behavior occurring across $\Delta\varepsilon_4$. The magnitude of $\Delta\varepsilon_4$ can be considered to be the "amount" or level of unloading superelasticity exhibited by a material. Notably, the unloading superelasticity quantified by $\Delta\varepsilon_4$ is smaller, and occurs and a lower stress, as compared to the loading superelasticity quantified by $\Delta\varepsilon_2$. This disparity between loading and unloading behavior is a feature of superelastic materials.

A pseudoelastic material may return to its previous shape after the removal of even relatively high applied strains by heating. For example, even if the secondary or daughter domain boundaries do become pinned, for example due to dislocations associated with plasticity, the material may be reverted to the primary or parent phase by stresses generated through heating.

Pseudoelasticity is generally exhibited in shape memory alloys. Pseudoelasticity and shape memory both arise from the reversible motion of domain boundaries during the phase transformation, rather than just bond stretching or the introduction of defects in the crystal lattice. Examples of shape memory materials include iron-chrome-nickel, iron-manganese, iron-palladium, iron-platinum, iron-nickel-cobalt-titanium, iron-nickel-cobalt-tantalum-aluminum-boron, copper-zinc-aluminum, copper-zinc-aluminum-nickel, copper-aluminum-nickel, and nickel-titanium alloys. Shape memory materials can also be alloyed with other materials including zinc, copper, gold, and iron.

Shape memory materials are presently used in a variety of applications. For example, a variety of military, medical, safety and robotic applications for shape memory materials are known. Medical grade shape memory materials are used for orthodontic wires, guide wires to guide catheters through blood vessels, surgical anchoring devices and stent applications, for example. One shape memory material in wide use, particularly in medical device applications, is a nickel-titanium shape memory material known as "Nitinol".

Many medical grade shape memory wire products are made of biocompatible implant grade materials including "NiTi" materials. As used herein, "nickel-titanium material", "nickel-titanium shape memory material" and "NiTi" refer to the family of nickel-titanium shape memory materials including Nitinol (an approximately equiatomic nickel-titanium, binary shape memory material) as well as alloys including nickel and titanium as primary constituents but which also include one or more additional elements as secondary constituents, such as Nitinol tertiary or quaternary alloys (e.g., Nitinol with additive metals such as chromium, tantalum, palladium, platinum, iron, cobalt, tungsten, iridium and gold).

Wire products made of shape memory materials are manufactured by forming a relatively thick piece of hot-worked rod stock from a melt process. The rod stock is then further processed into wires by drawing the rod stock down to a thin diameter wire. During a drawing process, often referred to as a "cold working" process, a wire is pulled through a lubricated die to reduce its diameter. The deformation associated with wire drawing increases the stress in the material, and the stress eventually must be relieved by various methods of heat treatment or annealing at elevated temperatures to restore ductility, thus enabling the material to undergo further cold working to further reduce the wire diameter. Each time the wire is annealed to enable further cold working, the accumulated internal stress—and therefore, the accumulated cold work—is "reset" to a zero level. These iterative processes of cold working and annealing may be repeated several times before a wire of a desired diameter is produced and processing is completed.

Although pseudoelastic wires made in accordance with foregoing processes may demonstrate desirable material properties for in vivo use, such wires are not generally radiopaque, i.e., the material of the wire allows X-rays or other types of radiation to pass through and therefore the wire material is not sufficiently distinguishable from surrounding anatomic structures in X-ray images. Substantial design efforts have been focused on imputing radiopacity to in vivo wire materials, such as by creating composite wires which utilize a radiopaque core material surrounded by a biocompatible sleeve suitable for in vivo use. Where in vivo wires are made radiopaque, X-ray imaging equipment can be used to assess, verify and/or monitor the location of the wire within the patient's body.

A primary constituent material of NiTi wires is nickel, as noted above. In some instances, it may be desirable to avoid the use of nickel for implanted medical devices, thereby minimizing any chance for adverse in vivo reactions in nickel-sensitive patients.

SUMMARY

The present disclosure relates to Ti—Nb—Hf/Zr—(Cr) alloy shape-memory wires suitable for use in medical devices and actuators, and methods for manufacturing such wires. The present shape-memory Ti—Nb—Hf/Zr—(Cr) alloy is a superelastic wire material particularly suited for in vivo applications. For example, the present Ti—Nb—Hf/Zr—(Cr) alloy wire is radiopaque, thereby enabling surgical use of a monolithic, shape-memory alloy wire while preserving the ability to monitor the in vivo location of the wire through X-ray or other radiation-based imaging systems. In addition, the present Ti—Nb—Hf/Zr—(Cr) alloy can be manufactured to exhibit shape-memory alloy material properties without the use of nickel as an alloy constituent, thereby accommodating nickel-sensitive patients. The present Ti—Nb—Hf/Zr—(Cr) alloy can also be processed to exhibit a martensite/austenite transformation temperature near body-temperature, i.e., 37° C., so that shape-memory effects can be utilized to accomplish work in vivo.

In one form thereof, the present invention provides a shape-memory wire for a medical device, the wire including titanium, niobium and at least one of hafnium and zirconium, the wire exhibiting superelastic behavior and having an austenitic finish temperature less than 37° C.

In another form thereof, the present invention provides a method for producing a shape-memory wire for a medical device, the method including: imparting between 50% and 99% cold work to a wire including titanium, niobium and at least one of hafnium and zirconium, such that a resulting cold worked wire construct has a final diameter of less than 10 mm; and shape-setting the cold-worked wire construct by annealing the cold worked wire construct at between 400° C. (673 K) and 1000° C. (1273 K) for a period of at less than 120 seconds, the shape-setting step performed while a stress is applied to the wire construct.

BRIEF DESCRIPTION OF THE DRAWINGS

The above-mentioned and other features of the disclosure, and the manner of attaining them, will become more apparent and will be better understood by reference to the following description of embodiments of the invention taken in conjunction with the accompanying drawings, wherein.

Corresponding reference characters indicate corresponding parts throughout the several views. The exemplifications set out herein illustrate embodiments of the disclosure and such exemplifications are not to be construed as limiting the scope of the invention in any manner.

DETAILED DESCRIPTION

Figure 1:
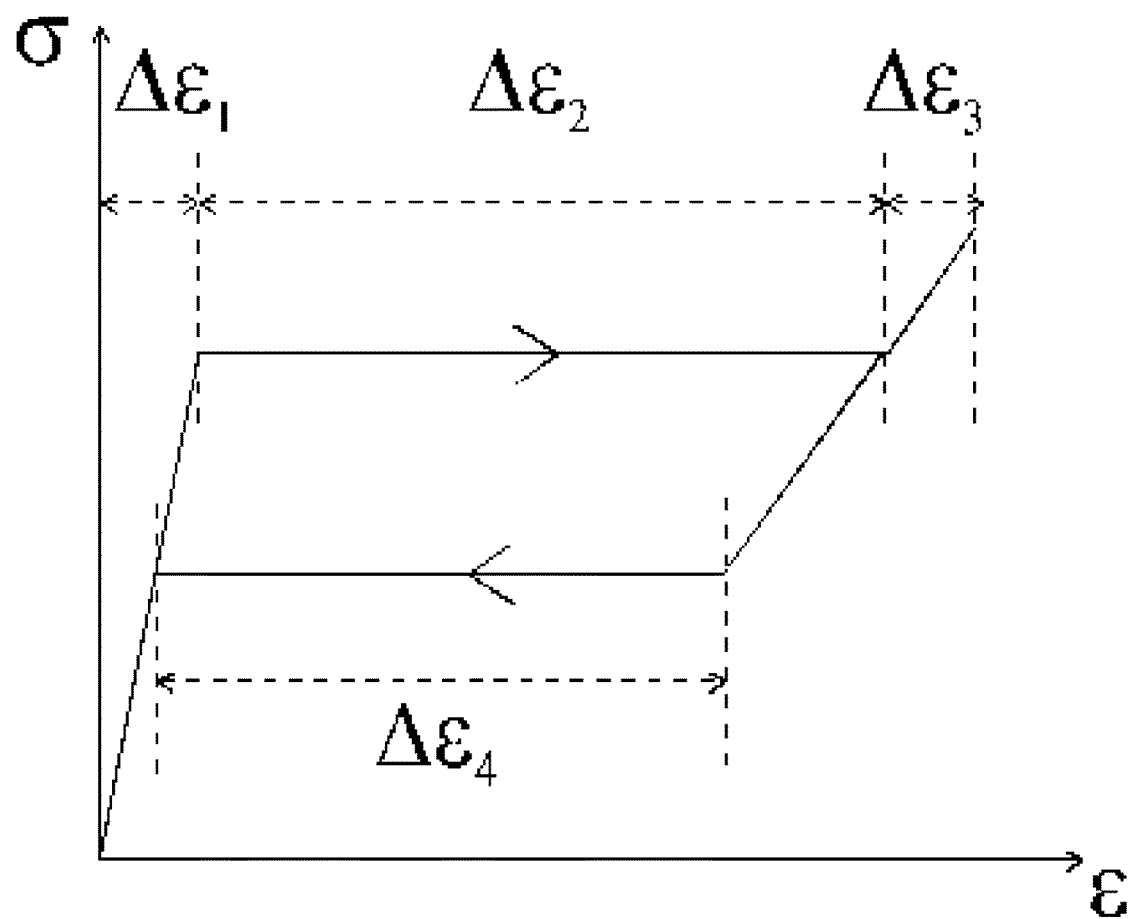
FIG. 1 is a schematic stress-strain curve for a superelastic material.

The present disclosure relates to shape memory wire products, and medical devices including shape memory wire products, such as round and flat wire, strands, cables, coils, and tubing, made from a shape memory material or alloy. These wire products are formed from a titanium-niobium-hafnium/zirconium metal alloy, and may further include other alloying elements such as chromium. Thus, the material may be referred to herein as Ti—Nb—Hf, Ti—Nb—Zr, Ti—Nb—Hf/Zr, or Ti—Nb—Hf/Zr—(Cr) (where chromium is in parens to indicate its optional status of a constituent of the alloy). As described in detail below, the wire is processed to produce products exhibiting a low modulus of elasticity, superelastic behavior, and shape memory behavior in body-temperature environments.

In an exemplary embodiment, titanium-niobium-hafnium/zirconium (Ti—Nb—Hf/Zr) alloys made in accordance with the present disclosure include titanium present at 30-70 wt. %, niobium present at 15-35 wt. %, and hafnium and/or zirconium present at 11-31 wt. %. Hafnium and Zirconium are considered to be interchangeable in the present alloy, in that one can be substituted for the other in any amount up to the total constituency of Hf/Zr. For example, for an alloy including 21 wt. % hafnium/zirconium, the alloy may include 21 wt. % hafnium, 21 wt. % zirconium, or any combination of hafnium and zirconium totaling 21 wt. % (e.g., 1 wt. % Hf and 20 wt. % Zr, 11 wt. % Hf and 10 wt. % Zr, etc.). Moreover, zirconium is similar to hafnium and is present in commercially pure hafnium. Thus, while it is contemplated that a wire made in accordance with the present disclosure may exclude zirconium, it is also contemplated that zirconium may replace any portion of the hafnium constituent of the wire while maintaining a material system suitable for use in medical or actuator devices as described below.

Depending on the wire application and particular needs of the user, the relative constituencies of each material may be varied.

The amount of titanium in the present Ti—Nb—Hf/Zr alloy may be as little as 30 wt. %, 40 wt. %, or 50 wt. % and as much as 56 wt. %, 60 wt. %, or 70 wt. %, or may be any value within any range defined by any of the foregoing values. The amount of niobium in the present Ti—Nb—Hf/Zr alloy may be as little as 15 wt. %, 20 wt. %, or 22 wt. % and as much as 28 wt. %, 30 wt. %, or 35 wt. %, or may be any value within any range defined by any of the foregoing values. The amount of hafnium and/or zirconium in the present Ti—Nb—Hf/Zr alloy may be as little as 11 wt. %, 16 wt. %, or 18 wt. % and as much as 24 wt. %, 26 wt. %, or 31 wt. %, or may be any value within any range defined by any of the foregoing values.

In one exemplary embodiment, wire in accordance with the present disclosure is made from a ternary Ti-25Nb-21Hf alloy (i.e., 25 wt. % niobium, 21 wt. % hafnium, and balance titanium at 54 wt. %). In another exemplary embodiment, wire in accordance with the present disclosure is made from a quaternary Ti-24.8Nb-16.2Hf-1Zr alloy (i.e., 24.8 wt. % niobium, 16.2 wt. % hafnium, 1 wt. % zirconium and balance titanium at 58 wt. %).

Chromium may optionally be alloyed with wire in accordance with the present disclosure. The amount of chromium in a Ti—Nb—Hf/Zr—Cr alloy may be as little as 0.05 wt. %, 0.2 wt. %, or 0.4 wt. % and as much as 0.6 wt. %, 0.8 wt. %, or 1 wt. %, or may be any value within any range defined by any of the foregoing values.

The present alloy may exhibit austenite and martensite phases based on temperature. When in the austenite phase, upon cooling the material begins to transform to martensite at the martensite start ($M_S$) temperature with complete transformation to martensite occurring by the martensite finish ($M_F$) temperature. Upon heating from the martensite phase, the material begins to transform to austenite at the austenite start ($A_S$) temperature with complete transformation to austenite occurring at the austenite finish ($A_F$) temperature. Of particular interest in the field of medical devices are alloys having ingot or active austenitic finish temperatures ($A_F$) less than body temperature, i.e., less than about 37° C.

Exemplary manufacturing processes by which wires may be made in accordance with the present disclosure are set forth in Section I below, and general descriptions of the resulting physical characteristics of wires made in accordance with the present process are set forth in Section II below. Working Examples are set forth in Section III below. Applications using wires made in accordance with the present disclosure are set forth in Section IV below.

As discussed in detail in Section IV below, shape memory wire made in accordance with the present disclosure may be used in medical devices such as, for example, implantable cardiac pacing, shocking and/or sensing leads, implantable neurological stimulating and/or sensing leads, wire-based stents, medial guidewires, catheters, blood filter devices, or any other medical device application in which a shape memory or superelastic characteristic is desired. Wire products produced in accordance with the present disclosure may also be used in non-medical device applications in which a shape memory or superelastic characteristic is desired, for example in shape memory actuator applications which utilize the shape transformation of the wire material at a given temperature to impinge upon and/or move an adjacent structure.

As used herein, "wire" or "wire product" encompasses continuous wire and wire products which may be continuously produced and wound onto a spool for later dispensation and use, such as wire having a round cross section and wire having a non-round cross section, including flat wire or ribbon. "Wire" or "wire product" also encompasses other wire-based products such as strands, cables, coil, and tubing, which may be produced at a particular length depending on a particular application. In addition to wire and wire product, the principles of the present disclosure can be used to manufacture other material forms such as rod materials having a diameter of less than 5 mm and thin material sheets.

I. DESCRIPTION OF THE PRESENT MANUFACTURING PROCESS

An exemplary process for producing superelastic Ti—Nb—Hf/Zr—(Cr) is described in detail below. Briefly, this exemplary process includes first procuring a "coarse" wire material that is fully annealed. This coarse wire material forms the starting point for processing in accordance with the present disclosure, and may be produced from an ingot by an iterative drawing/annealing process as described below.

The coarse wire is then drawn to a fine wire diameter of 10 mm or less without intervening annealing. This drawing process introduces a large amount of cold work and associated internal stresses within the wire material, which are not "reset" by a full annealing process.

Instead, the cold-worked wire is subjected to a shape setting process in which the wire is formed into a desired shape or otherwise placed under load, then partially annealed to only slightly relieve the cold work and internal stresses. The resulting wire exhibits superelastic behavior in a nickel-free and radiopaque construct which exhibits shape-memory transition behavior at body temperature.

1. Wire Preparation

Initial preparation of a wire may involve first forming a piece of rod stock, for example, based on conventional melt processing techniques, followed by one or more iterations of warm or hot working, such as by forging or extrusion, and conventional iterative cold working and annealing.

For example, an ingot may be melted using an arc-melting, cold crucible technique in order to cast rods having a diameter larger than the coarse wire. These rods can then be hot extruded, such as at about 900° C., in order to effect a large area reduction (e.g., 8:1) to create intermediate rod stock. Full annealing may optionally be performed after hot working to achieve equiaxed microstructure. These extruded rods are then drawn by cold-drawing techniques described herein to create the coarse wire structure.

The cold work process imparts cold work which is stored in the material microstructure, as further described herein. By contrast, the iterative drawing/annealing process to reduce the diameter of the rod stock from its as-formed diameter to an initial wire diameter is accomplished by fully annealing the material between draws. In full annealing, the cold-worked material is heated to a temperature sufficient to substantially fully relieve the internal stresses stored in the material and regrow the material grains to their pre-processing mean grain size, thereby relieving the stored cold work and "resetting" cold work to zero.

In materials in accordance with the present disclosure, full annealing is accomplished at a temperature about 700° C. for at least 30 minutes. Alternatively, a full anneal can be accomplished with a higher temperature, such as between 900° C. and 1200° C., for a shorter time, such as between 10 seconds and 10 minutes. Of course, a relatively higher temperature annealing process can utilize a relatively shorter time to achieve a full anneal, while a relatively lower temperature will typically utilize a relatively longer time to achieve a full anneal. Whether a full anneal has been accomplished can be verified in a number of ways as well known in the art, such as microstructural examinations using scanning electron microscopy (SEM), mechanical testing for ductility, strength, elasticity, etc., and other methods.

Figure 2A:
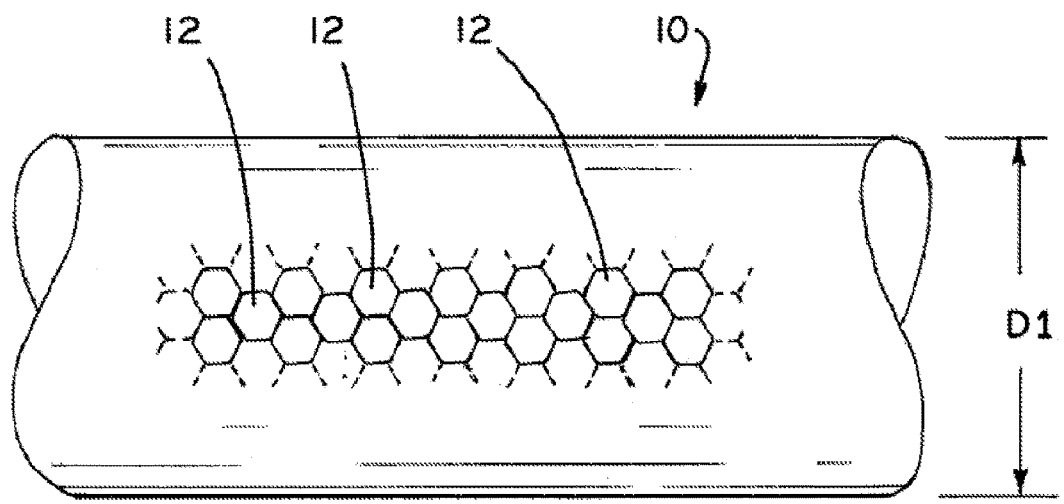
FIG. 2A is a schematic view of a portion of wire having an equiaxed grain structure.

Referring now to FIG. 2A, a schematic or exaggerated view of a portion of wire 10 manufactured in accordance with conventional cold working and annealing techniques is shown. Wire 10 has been subjected to one or more, perhaps several or a very large number of, iterations of conventional cold working and annealing, as described above, to form an equiaxed crystal structure within the material of wire 10. FIG. 2A illustrates representative full-size, equiaxed crystals 12 in the material of pre-processing wire 10.

As used herein, "equiaxed" refers to a crystal structure in which the individual crystals 12 have axes that are approximately the same length, such that the crystals 12 collectively have a large number of slip planes, leading to high strength and ductility. For purposes of the present disclosure, ductility is defined as the strain capacity of a material to rupture, as measured by a monotonic tensile test with a gauge length exceeding 250× the diameter or thickness of the wire at a temperature of 298±5K. Material strength includes yield ultimate tensile strength (i.e., the level of stress the material will bear prior to rupture) and yield strength (i.e., the level of stress the material will bear prior to a specified amount of plastic deformation). However, it is not necessary that the grain structure be equiaxed in order to process the wire into the finished product described herein. The grain structure may, for example, contain deformed grains that have been recovered to the parent phase through a high temperature anneal process described herein.

When the above processing is complete, the resulting coarse wire is ready for further processing to create a wire product which exhibits superelastic and/or shape memory behavior as described in detail below. Although the exemplary embodiment shown and described herein is focused on a wire construct, it is contemplated that the process may also be employed to create other constructs using the same principles. Alternative constructs include strips of flat material and hollow tube materials. In addition, although a round wire is shown in the drawings of FIGS. 2A, 2B, 3 and 4, other cross-sectional wire geometries may be created (e.g., square, rectangular, or other polygonal).

2. Thermomechanical Processing to Impart Superelasticity and/or Shape Memory

Figure 2B:
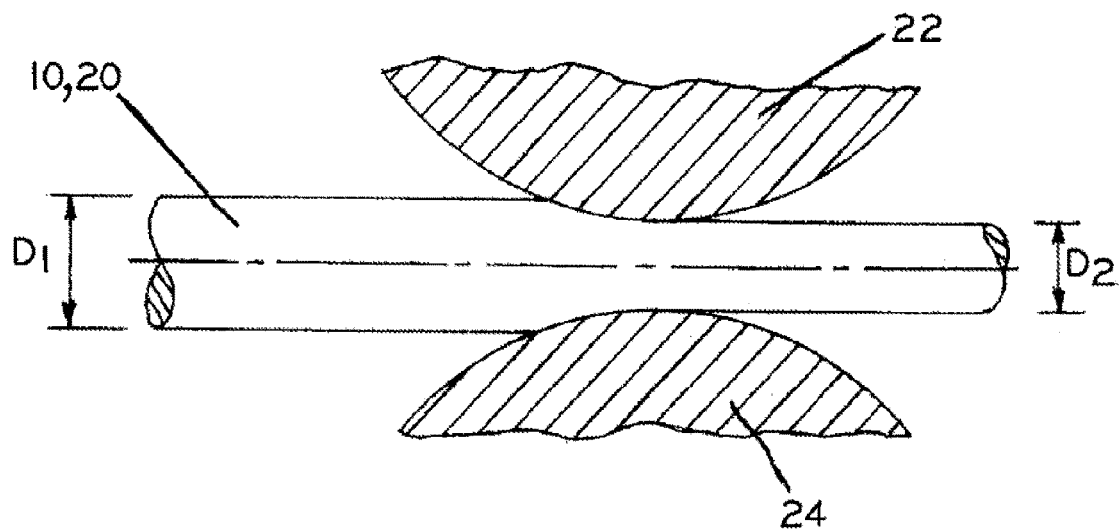
FIG. 2B is a schematic view illustrating an exemplary forming process of monolithic wire using a lubricated drawing die.
Figure 3:
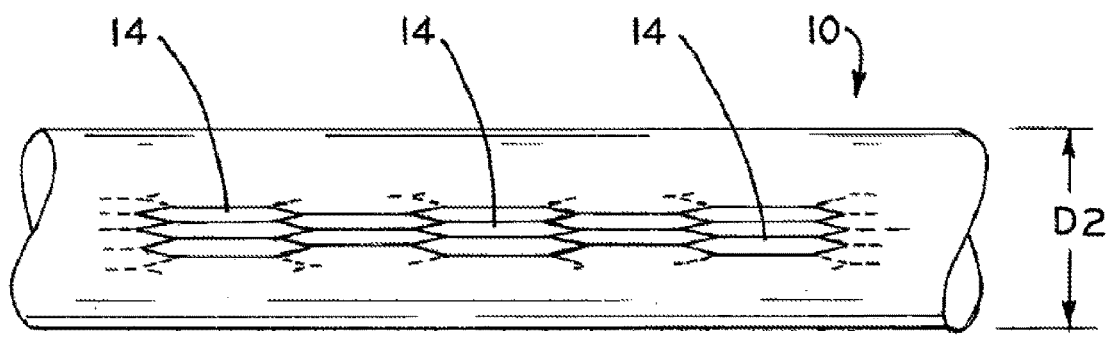
FIG. 3 is a schematic view of the portion of wire of FIG. 2 having an elongated grain structure after cold work conditioning in accordance with an embodiment of the present process.

Referring now to FIG. 2B, prior to the final shape-setting anneal, wire 10 is subjected to cold work in the form of a cold work conditioning step. As used herein, "cold work conditioning" means imparting a relatively large amount of cold work to a material, such as by wire drawing, swaging, or otherwise forming. In the illustrated embodiment, the cold work conditioning step is performed by drawing wire 10 through lubricated dies 22,24 (FIG. 2B) defining an output diameter $D_2$, which is less than the initial diameter $D_1$ of the undrawn wire 10 shown in FIG. 3. In one exemplary embodiment, the cold work conditioning step by which the diameter of wire 10 is reduced from $D_1$ to $D_2$ is performed in a single draw and, in another embodiment, the cold work conditioning step by which the diameter of wire 10 is reduced from $D_1$ to $D_2$ is performed in multiple draws which are performed sequentially without any annealing step therebetween. The lack of an intervening annealing step causes cold work to "accumulate" in the wire material, rather than being reset to zero as is done with the iterative draw/anneal pre-processing as described above. Such "accumulated" cold work, whether imparted by a single drawing step or multiple draws, is calculated by the following formula, where $D_2$ is the wire diameter after the cold-work draw or draws is complete and $D_1$ is the wire diameter before the cold-work draw or draws have begun:

$$cw = 1 - \left(\frac{D_2}{D_1}\right)^2$$

Further discussion of exemplary cold work conditioning processes are presented in U.S. Patent Application Publication No. 2010/0075168, entitled FATIGUE DAMAGE RESISTANT WIRE AND METHOD OF PRODUCTION THEREOF, filed Sep. 18, 2009, and assigned to the present assignee, the disclosure of which is hereby expressly incorporated by reference herein in its entirety. The foregoing reference also discloses methods of limited annealing following the cold work conditioning to create a nanograin microstructure, which may optionally be applied to wires made of the alloy systems described herein.

In an exemplary embodiment, cold work between 90% and 99% is used to reduce the coarse Ti—Nb—Hf/Zr—(Cr) wire material to a finished wire diameter $D_2$ of up to 10 mm, and prepare the material for a final shape-set anneal. Depending on the particular wire characteristics desired, cold work may be as little as 50%, 75%, or 90% and as much as 99% 99.9%, or may be any value within any range defined by any of the foregoing values. The final wire diameter may be any desired diameter as required or desired for a particular application, and in certain exemplary embodiments may be as small as 0.05 mm, 0.1 mm or 0.5 mm and as large as 2 mm, 5 mm or 10 mm, or may be any diameter within any range defined by any of the foregoing values.

Figure 4:
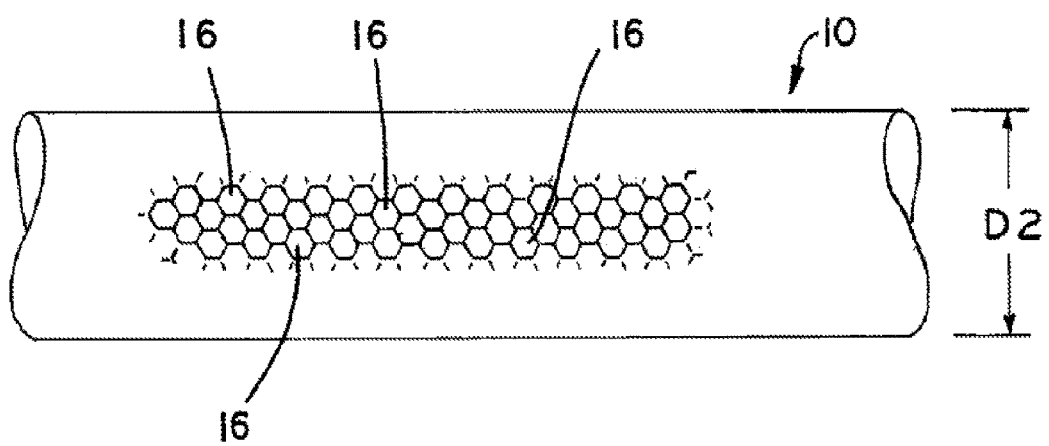
FIG. 4 is a schematic view of the portion of wire of FIG. 3 having an equiaxed grain structure with smaller grains than the equiaxed grain structure of the wire in FIG. 2A after recrystallization in accordance with an embodiment of the present process.

The cold-worked wire 10, after having been drawn to the desired finished diameter $D_2$, undergoes a shape setting annealing process in which it is annealed under tension sufficient to hold the wire in a substantially linear configuration, or constrained in a specific non-linear shape to effect a final desired geometry. The heating of the wire during the shape-set annealing process allows formation of a new crystallographic structure having crystals 16, as shown in FIG. 4. Crystals 16 may comprise nano-scale equiaxed crystals, though creation of such equiaxed or nanograin crystal microstructure is not required to impart the shape-memory and/or superelastic qualities described herein.

In the present process, shape set annealing occurs at a temperature between 400° C. (673 K) and 1000° C. (1273 K) for a period less than 120 seconds, with the particular combination of temperature and time chosen to restore a majority of the wire material to the parent material phase. In the case of thin wire sections, e.g., less than 2 mm, this heat treatment step can be accomplished in less than 10 seconds, while for larger diameter wires, e.g., between 2 mm and 10 mm, this heat treatment step may take up to 10 minutes.

As also described above with respect to the full annealing process, temperature and time in the shape-setting anneal are interdependent, inversely correlated variables. That is, a higher temperature results in a shorter annealing time, while a lower temperature results in a longer annealing time to achieve the same result. Exemplary time/temperature combinations which produce superelastic Ti—Nb—Hf/Zr—(Cr) wires in accordance with the present disclosure, after cold working as described above, include: 500° C. (773 K) for between 10 seconds and 1 minute; 650° C. (823 K) for between 1 second and 30 seconds; and 750° C. (923 K) for between 0.1 seconds and 10 seconds. One particular shape setting process suitable for wire having a diameter of about 1-2 mm, which produces strong superelastic behavior, is 650° C. (823 K) for about 3 seconds. As noted above, any combination of parameters may be chosen for a particular product within the scope the present disclosure, provided the annealing process restores a majority of the wire to the parent phase.

After the shape set anneal is complete, the material is cooled in an inert atmosphere to room temperature (i.e., about 21° C.). Such cooling may occur in air or liquid.

During the shape set anneal, the wire is held under stress. For example, the wire may be placed and held in axial tension during the annealing process, which "trains" the finished wire into a linear configuration that will again elongate when heated past the transformation temperature. Of course, any desired finished shape may be chosen for a particular wire construct as required or desired for a particular design. For example, the wire may be coiled or otherwise curved or bent into a non-linear shape to place the material under stress during the shape set anneal.

II. DESCRIPTION OF PROPERTIES OF WIRES MADE IN ACCORDANCE WITH THE PRESENT MANUFACTURING PROCESS

The modulus of elasticity of the present Ti—Nb—Hf/Zr—(Cr) material is between 50 GPa and 80 GPa, which is advantageously comparable to Nitinol and less than most beta titanium alloys which fall in the 90-110 GPa range.

The present Ti—Nb—Hf/Zr—(Cr) wire material the wire also exhibits a total isothermally recoverable strain, as measure at body temperature (i.e., 37° C. or 310K) of greater than 3%. In some instances, isothermally recoverable strain is greater than greater than 4%. Wire made in accordance with the present disclosure has at least 2% isothermally recoverable strain as measured at body temperature.

Figure 7A:
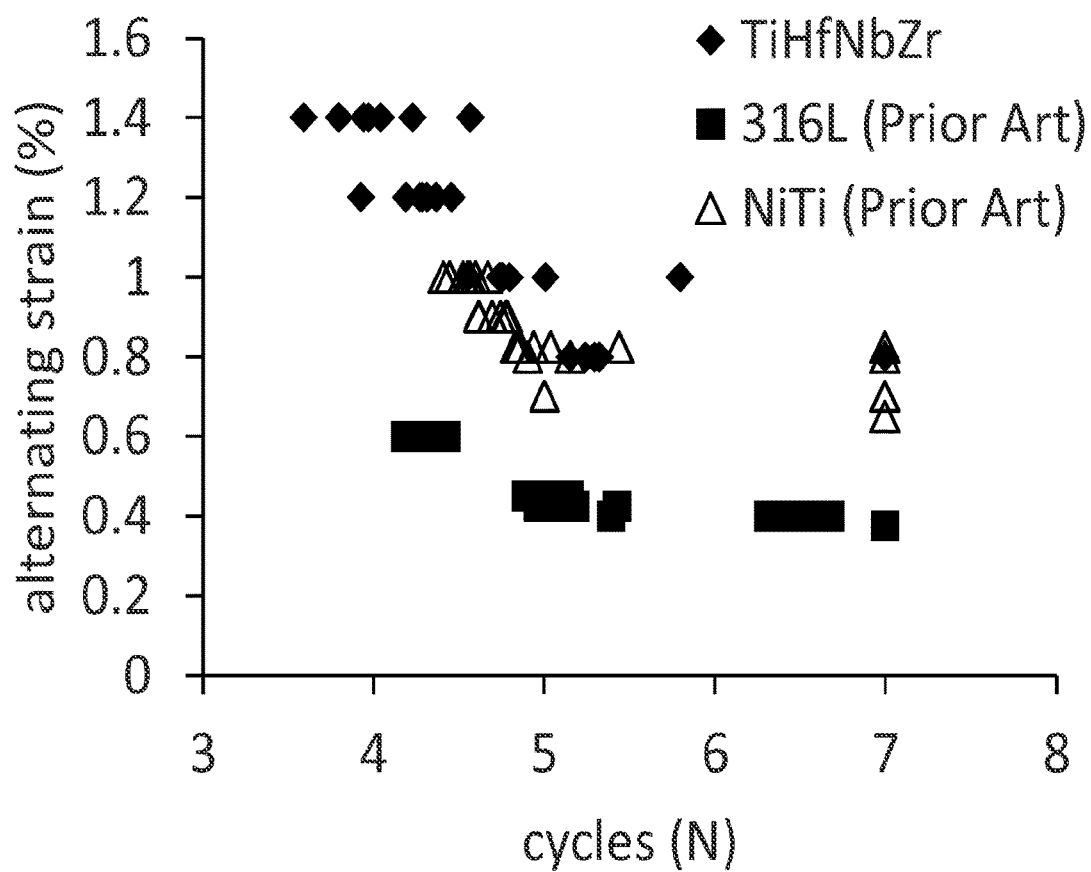
FIGS. 7A and 7B are graphs illustrating fatigue life vs. alternating strain level for a wire made in accordance with the present disclosure, a wire made of 316L stainless steel, and a wire made of NiTi.

Testing for recoverable strain can be performed as a uniaxial tensile test at a particular temperature. In FIG. 7C, samples of wire made in accordance with the present disclosure were tested at a temperature T equal to 37° C.±5° C. (310K±5K) for the samples shown by solid and dashed lines, while a temperature of 150° C.±5° C. (423±5K) was used for a sample shown in dotted lines.

Moreover, the above-described process can be used to produce wire materials with an austenitic finish temperature $A_F$ less than 37° C., as demonstrated in FIG. 7C, which advantageously ensures that phase transformation and, therefore, shape-memory behavior, will occur between room temperature (i.e., about 21° C.) and body temperature (i.e., about 37° C.). This phase transformation can be used to effect work inside a patient's body with an implanted wire structure, such as a stent which expands as it is warmed to body temperature after initial implantation at an arterial site.

The present Ti—Nb—Hf/Zr—(Cr) also demonstrates high fatigue life characteristics. Flex fatigue capability, denoted by the alternating strain level that the wire is capable of withstanding at 10 million cycles, has been shown to be about 0.8% strain, which is advantageously comparable to superelastic NiTi wire.

Figure 7B:
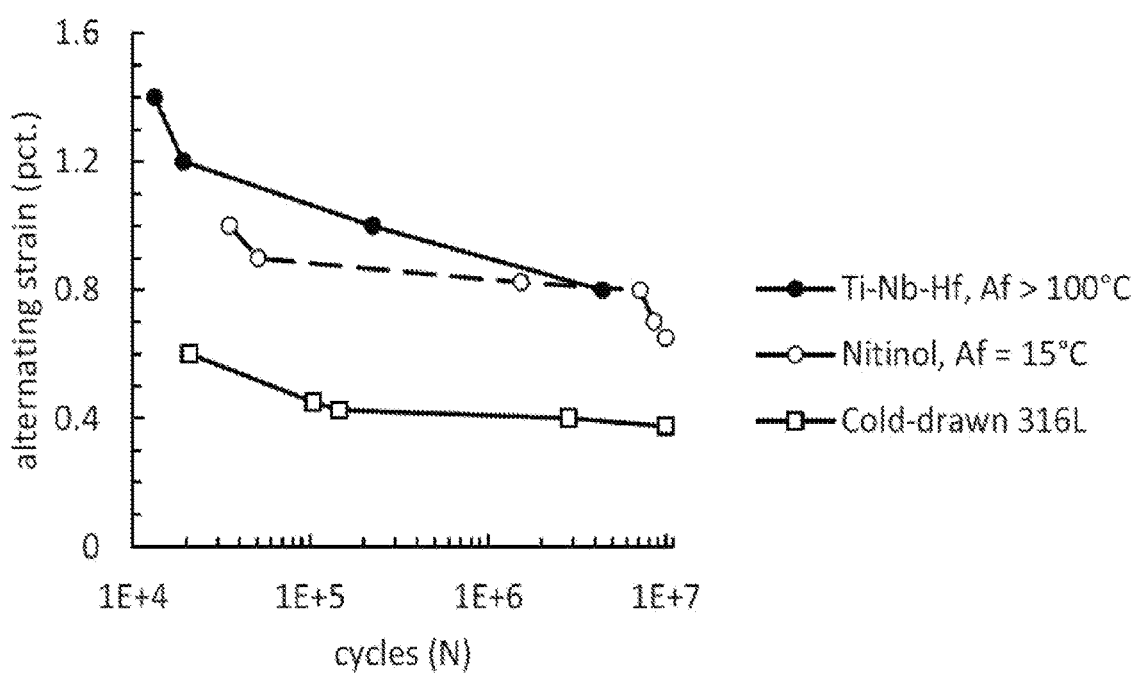
Figure 7C:
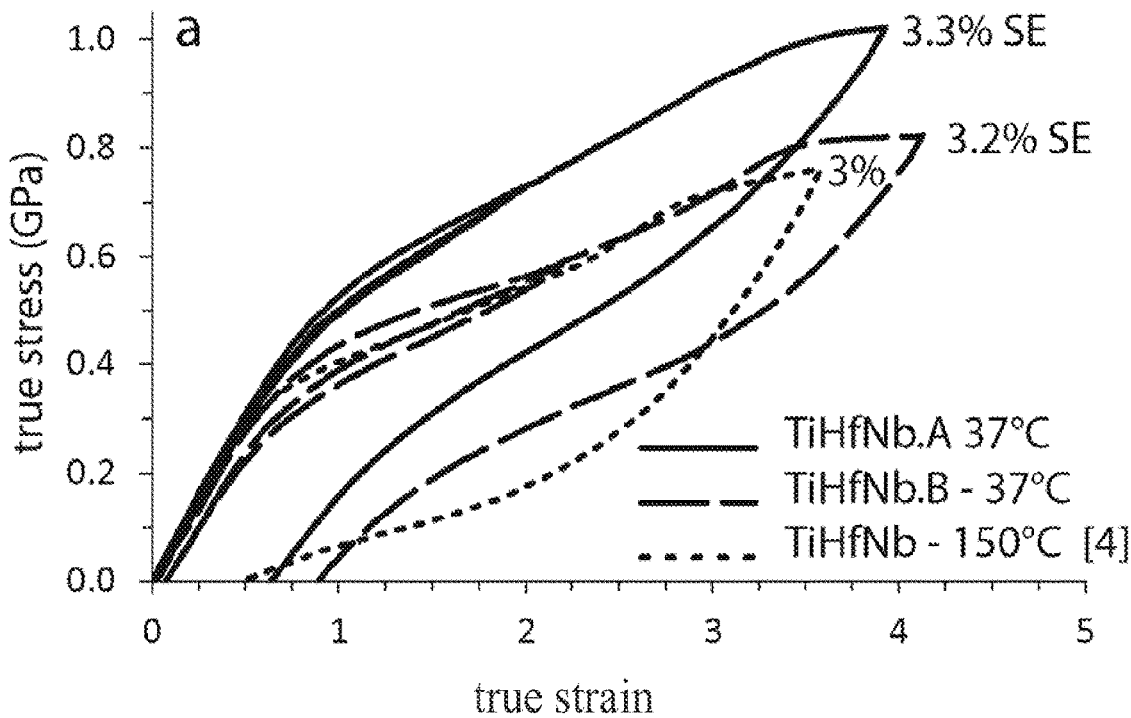
FIGS. 7C and 7D are graphs illustrating stress vs. strain for wires made in accordance with the present disclosure.

FIG. 7B illustrates results of rotary beam fatigue testing of the Ti—Nb—Hf/Zr—(Cr) material made in accordance with the present disclosure, as tested at room temperature. As illustrated, the present material is able to withstand larger nominal alternating strain percentages as compared to baseline NiTi and 316L stainless steel control materials where total cycles are in excess of $10^4$ and $10^5$ cycles. The present Ti—Nb—Hf/Zr—(Cr) material has been shown to outperform 316L stainless steel and performed similarly to the NiTi material at about $4 \times 10^6$ cycles. More particularly, the present material was found to survive greater than $10^4$ cycles at strain amplitudes of about 1.2% and 1.4%, greater than $2 \times 10^5$ cycles at strain amplitude of 1.0%, and greater than $4 \times 10^6$ cycles at a strain amplitude of 0.8%.

In addition, testing of the present material samples resulted in survival of the material for greater than $10^7$ cycles at fatigue strain amplitudes in excess of 0.5% in phosphate-buffered saline solution. Thus, the presence of the saline solution had a negligible impact on fatigue results, showing that the present Ti—Nb—Hf material has the requisite durability for service as a long-term, load-bearing in vivo device.

III. EXAMPLES

The following examples provide specific illustration to the general principles set forth above. The results achieved in the following examples are indicative of results achievable using the general processing methods described above.

1. Example 1—Ti—Nb—Hf Alloys 180 grams of a Ti-24.8Nb-21Hf-1Zr shape memory alloy was melted using an arc-melting, cold crucible technique in order to cast 12.7 mm diameter by approximately 150 mm length rods. These rods were hot extruded at 900° C. in order to effect an area reduction of 8:1 giving a process output diameter of about 4 mm.

These 4 mm extruded rods were then drawn by the cold-drawing techniques described above to a cold work level of greater than about 70% reduction of area to give a diameter of about 1.4 mm. This cold work-conditioned material was fully annealed by heating to 1200° C., holding for 18 seconds, and cooling to room temperature in an inert atmosphere. Subsequently, the 1.4 mm annealed material was again cold-drawn using the techniques described above to a final diameter of 0.125 mm, thereby imparting a total cold work of greater than 99% reduction of area to the fine wire section and conditioning the material for the thermal shape-setting process.

The shape-setting process was accomplished by applying an axial tension and heating to 650° C., holding for 3 seconds, and cooling in an inert atmosphere to room temperature of about 21° C.

The superelastic tensile properties of this wire were verified by tensile testing using an Instron load frame. Briefly, the wire was positioned in a 125 mm gage length and clamped at the ends using pneumatic grips. Tests were conducted by displacing the wire axially at a strain rate of 0.001/s to 1% strain and then returning to zero load. Upon reaching zero load the test was repeated to 2% strain, then to 3% strain and so on. Tests were conducted where the temperature of the test chamber and specimen were held at 37° C. and 150° C.

Figure 5:
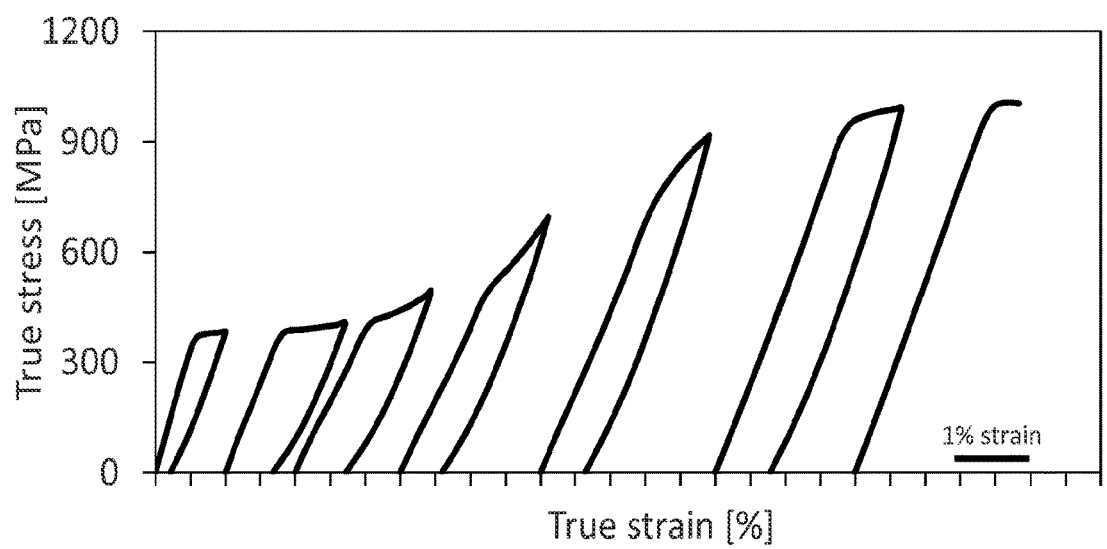
FIG. 5 is a graph illustrating stress vs. strain for a wire made in accordance with the present disclosure, in which the wire was serially subjected to varying, increasing levels of strain at a temperature of 37° C.

FIG. 5 illustrates a resulting stress-strain curve for the wire tested at the 37° C. temperature. As illustrated, the material underwent a forward stress-induced transformation from the parent high-temperature (austenite) phase to the daughter low-temperature (martensite) phase, however, upon load removal the material did not spontaneously recover the original shape.

Figure 6:
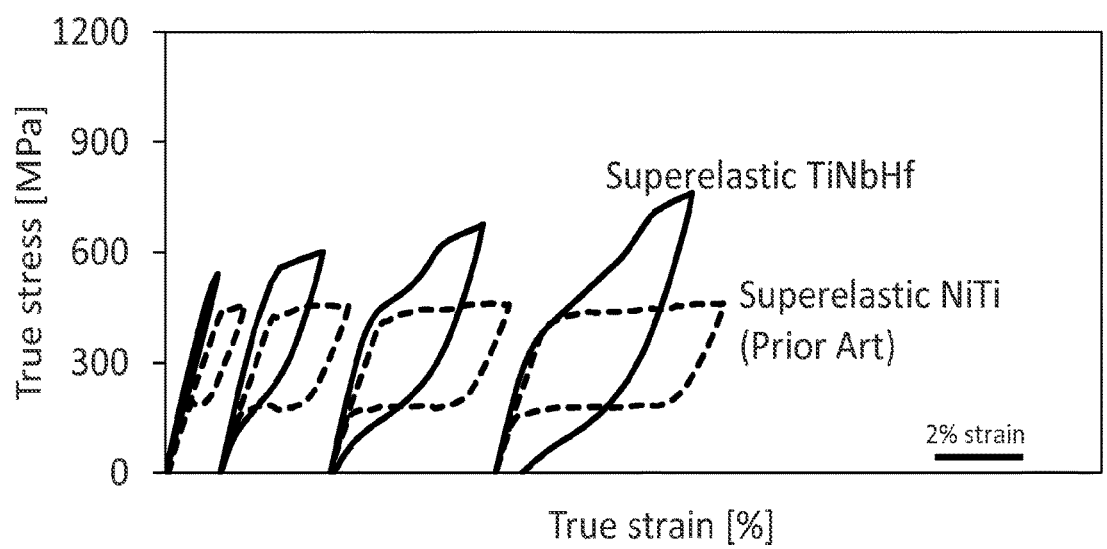
FIG. 6 is a graph illustrating stress vs. strain for a wire made in accordance with the present disclosure and a wire made of superelastic NiTi, in which each wire was serially subjected to varying, increasing levels of strain at a temperature of 150° C.

FIG. 6 illustrates a resulting stress-strain curve for the wire tested at the 150° C. temperature, juxtaposed against testing conducted on a straight annealed superelastic NiTi wire at a 37° C. temperature. As illustrated, the material exhibited both forward and reverse transformation upon loading and unloading respectively. A modulus of elasticity of less than 60 GPa and axial recoverable strain of greater than 3% were observed with stress hysteresis resembling a reversible stress-induced martensitic transformation at the test temperature of 150° C.

As noted above, adjustments to initial alloy chemistry, within the scope of the present disclosure, allow control over the transformation temperature to effect superelastic behavior over a temperature range of about −50° C. to a maximum of about 300° C., particularly including body temperature applications. Total maximum isothermally recoverable strain was measured at about 4% true strain.

Turning to FIG. 7A, fatigue testing of the material described above illustrates high fatigue strength as compared to control material including NiTi having an austenitic finish temperature of 15° C. and 316L stainless steel cold-drawn to impart cold work of 90%. The fatigue test data of FIG. 7 was gathered in ambient air at 300±5K at a test rate of 60 Hz using rotary beam, fully reversed, wire fatigue testing equipment as described in U.S. Patent Application Publication No. 2010/0075168, entitled FATIGUE DAMAGE RESISTANT WIRE AND METHOD OF PRODUCTION THEREOF, filed Sep. 18, 2009, and assigned to the present assignee, the disclosure of which is hereby expressly incorporated by reference herein in its entirety. As illustrated, the flex fatigue capability denoted by the alternating strain level at 10 million cycles, was located near 0.8% strain, which is similar to superelastic NiTi wire.

FIG. 7B illustrates further results of the rotary beam fatigue testing of the present material at room temperature. As illustrated, the present Ti—Nb—Hf material is able to withstand larger nominal alternating strain percentages as compared to the above-described NiTi and 316L control materials where total cycles are in excess of $10^4$ and $10^5$ cycles. The present material outperformed 316 stainless steel and performed similarly to the NiTi material at about $4 \times 10^6$ cycles. More particularly, the present material was found to survive greater than $10^4$ cycles at strain amplitudes of about 1.2% and 1.4%, greater than $2 \times 10^5$ cycles at strain amplitude of 1.0%, and greater than $4 \times 10^6$ cycles at a strain amplitude of 0.8%.

In addition, testing of the present material samples resulted in survival of the material for greater than $10^7$ cycles at fatigue strain amplitudes in excess of 0.5% in phosphate-buffered saline solution. Thus, the presence of the saline solution had a negligible impact on fatigue results, showing that the present Ti—Nb—Hf material has the requisite durability for service as a long-term, load-bearing in vivo device.

Further discussion of the material tested for the present Example is presented in a paper entitled "Potential Superelastic Nickel-Free Titanium Alloy," the entire disclosure of which is hereby incorporated herein by reference.

2. Example 2—Ti—Nb—Hf—Cr Alloys

A Ti—25 wt. % Nb—21 wt % Hf—0.5 wt % Cr alloy was produced. Wires having an outer diameter of 127 µm were made by drawing and annealing in accordance with the disclosure above. Samples of wires were cold worked at varying levels prior to a final anneal at 650° C. for a duration of 2 seconds.

FIG. 7C illustrates a resulting stress-strain curve for two wires tested at body temperature (i.e., about 37° C.), shown in solid and dashed lines respectively. These stress-strain curves are juxtaposed against a stress-strain curve for a Ti—Hf—Nb alloy wire made in accordance with Example 3, shown in a dotted line, tested at 150° C.

As shown in FIG. 7C, the present wires demonstrated superelastic strain characteristics at body temperature, in which superelastic behavior was observed for wires whose strain levels exceeded 4% and were recovered with residual strain of less than 1%. Thus, superelasticity of greater than 3% was observed in the present Example.

Figure 7D:
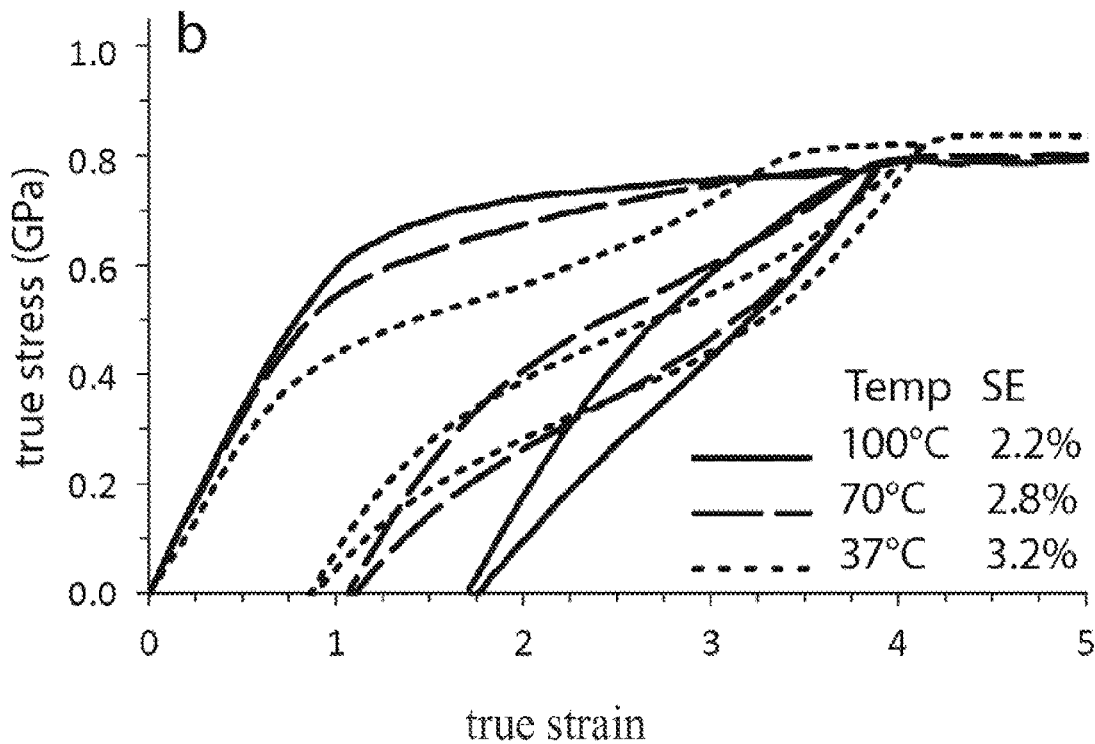

FIG. 7D shows another stress-strain curve for the wire of Ti—Hf—Nb—Cr wire shown in dashed lines in FIG. 7C, in which the wire was tested at body temperature (37° C., shown in dotted lines), 70° C. (shown in dashed lines) and 100° C. (shown in solid lines). As illustrated, each test demonstrated superelastic behavior in which residual strain subtracted from peak strain upon initial loading is greater than 2%. Specifically, this value was 2.2% for the 100° C. test sample, 2.8% for the 70° C. test sample, and 3.2% for the 37° C. test sample. Also shown in FIG. 7D is a second stress-strain curve resulting from a second loading of each wire, illustrating that the second loading of each wire results in a stress plateau commensurate with the initial loading.

Further discussion of the material tested for the present Example is presented in a paper entitled "Advances in Metallic Materials for Medical Devices," the entire disclosure of which is hereby incorporated herein by reference.

V. APPLICATIONS

Wires made in accordance with the present process may be used in applications including, but not limited to stents, guidewires (e.g., to guide catheters through blood vessels), aneurysm occlusion devices, heart wall closure devices, orthodontic wires and apparatuses, surgical anchoring devices, etc. Where such wires are used to replace NiTi, the Ti—Hf—Nb alloy material advantageously serves as a radiopaque, superelastic material which may be produced at reduced cost and with enhanced fatigue damage resistance.

Moreover, it is contemplated that the present Ti—Hf—Nb alloy systems have application potential wherever high-strength, low-modulus beta titanium alloys would be appropriate, including in applications such as guide wires, pacing wires, or stents where the low modulus, corrosion resistance, and high strain fatigue capability of the present alloy systems are leveraged in the absence of shape memory behavior.

Exemplary applications are detailed below.

1. Guide Wires

Figure 8:
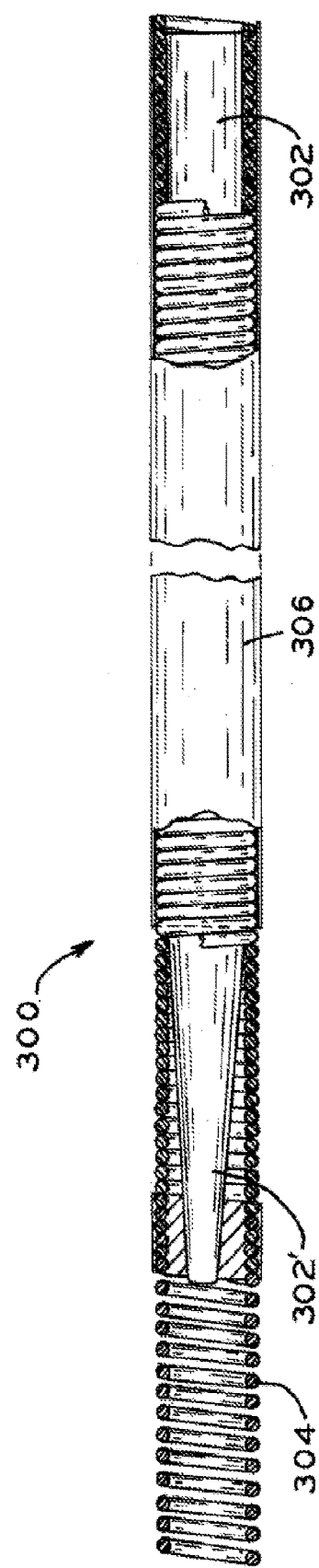
FIG. 8 is a partial section view of a guide wire in accordance with an embodiment of the present process.

Referring to FIG. 8, a percutaneous transluminal coronary angioplasty (PTCA) guide wire 300 is shown which comprises a metallic elongate wire 302 manufactured in accordance with the present process with tapered end 302'. Wire 302 is received within a coil wire 304, which in turn is received within a housing 306.

PTCA guide wires are used to access distal locations within the human body to treat vessel lesion in including, for example, atherosclerosis, or in order to facilitate implantation of a defibrillation electrode. In order to reach these locations, guide wires must flex sufficiently to navigate the anatomy en route to the target lesion or organ.

Figure 9:
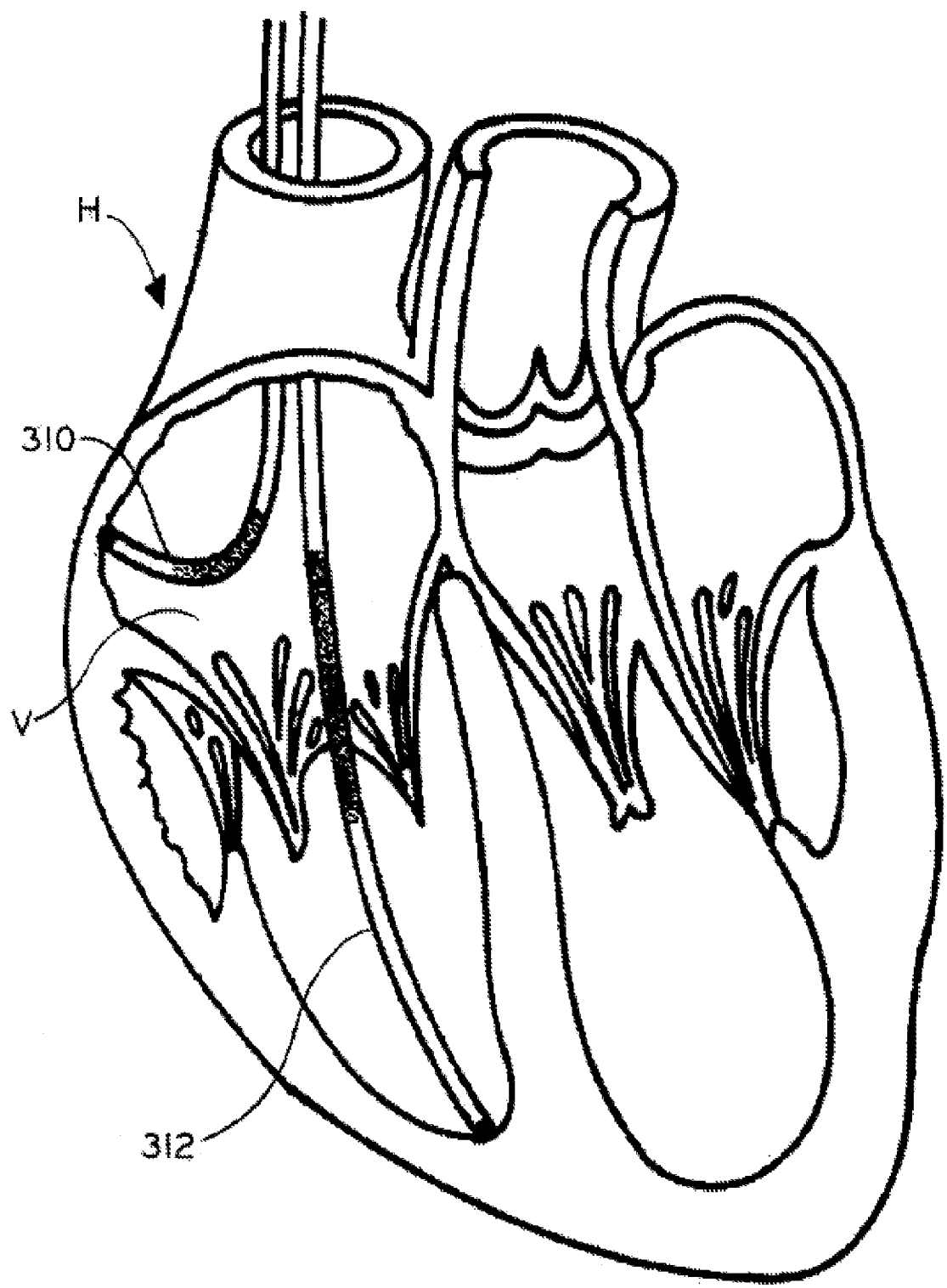
FIG. 9 is a partial section view of a heart, illustrating cardiac pacing leads received therein.

The elastic properties of the guide wire may be important in guide wire design because the wire should conform to the tortuous vessel anatomy as it is used to access various targeted locations for treatment within the body, such as the right ventricle of the heart as shown in FIG. 9.

The guide wire should successfully navigate the anatomy without suffering a material failure.

The present process provides a wire that possesses a high degree of flexibility due to a relatively high yield to ultimate strength ratio which is greater than 0.85, thereby imparting a relatively high yield strain to the guide wire. In some cases, a physician will manually shape the tip section of a guide wire in order to facilitate navigation of specific vessel anatomy. In this case, a material must possess the ability to both accept plastic deformation, in order to take a specific shape, and maintain good resilience to successfully move through the anatomy.

At the same time, the present process provides a wire that is radiopaque, so that the location and orientation of the guide wire within a patient's body is verifiable via medical imaging methods such as X-ray.

Wire 302 prepared in accordance with the present process provides a combination of superelastic behavior with radiopacity, thereby increasing the ability of wire 302 to withstand both pre-procedural, physician-planned plastic deformation and subsequent procedural elastic deformation en route to the target lesion, while also facilitating in vivo location of the wire via medical imaging.

2. Implantable Cardiac Pacing Wires

Figure 10:
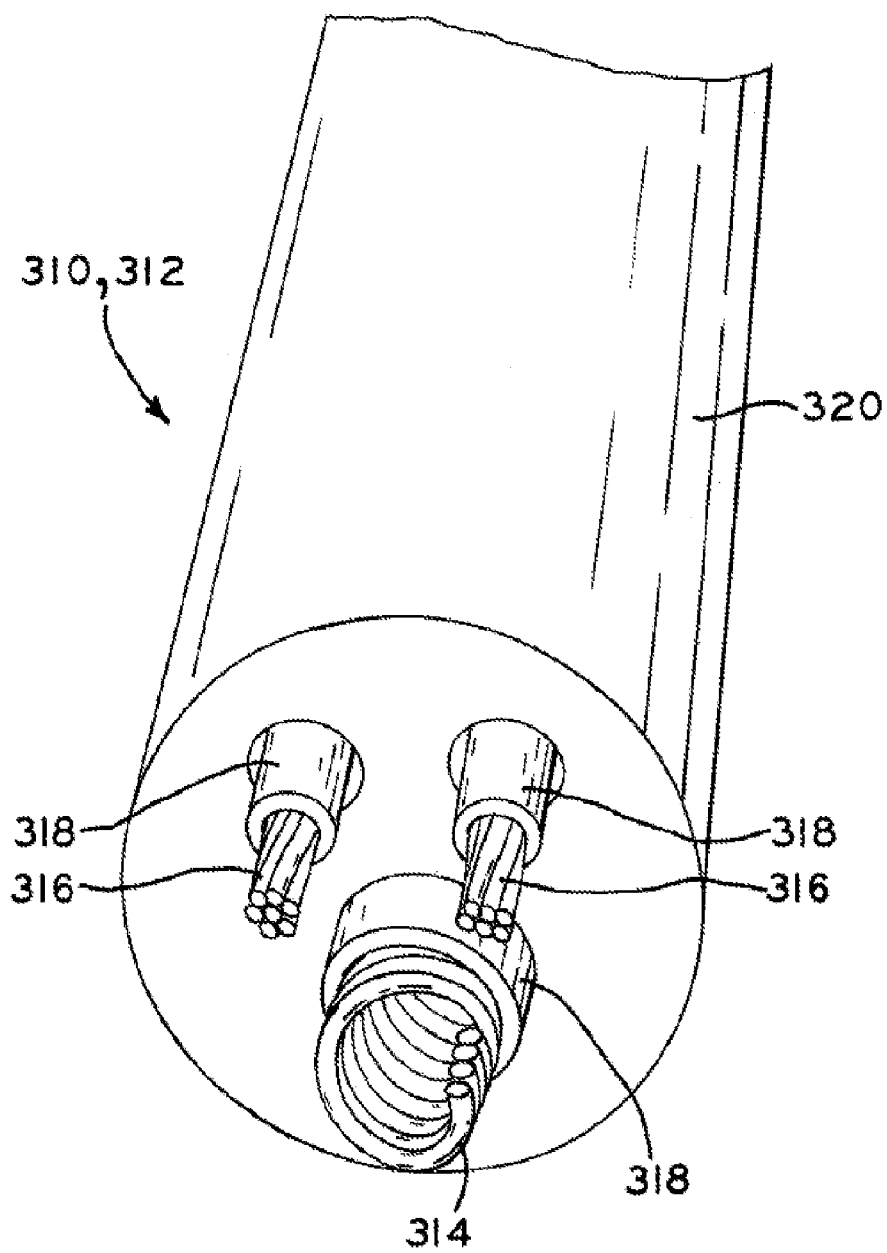
FIG. 10 is a section, perspective view of a cardiac pacing lead including wire made in accordance with the present process.

Referring to FIGS. 9 and 10, a first cardiac pacing lead wire 310 and second cardiac pacing lead wire 312 made in accordance with the present process are shown. Wires 310, 312 are utilized either singularly or in plurality in the form of a conductive braid, strand or microcable which is used to deliver therapeutic electrical signals to the heart.

Referring to FIG. 10, the cardiac pacing lead wires 310, 312 may comprise a combination of coiled wires 314 and/or microcable elements 316 which are overmolded and/or separated by an electrically insulating polymer sleeve 318 such as medical-grade polyurethane or silicone rubber. Sleeves 318 and wires 314, 316 are received within a housing 320.

Referring to FIG. 9, the lead is implanted within the right atrium and/or ventricle V of the heart H in order to deliver an electrical control signal thereby stimulating or otherwise providing pacing, defibrillation or cardiac resynchronization therapy in order to treat bradycardia, tachycardia, or other arrhythmias of the heart.

Within the spirit of this disclosure, dependent upon the intended therapy and patient physiology, lead wires 310, 312, or similar systems utilizing wires made in accordance with the invention may also be implanted with electrical connection to the outside of the heart the left atrium and the left ventricle. Required material characteristics are generally similar to those described earlier.

It is advantageous that pacing lead wires 310, 312 be substantially resistant to cyclic mechanical fatigue damage which is generally associated with the spatial displacement of the lead system with each beat of the heart at an average rate of up to 2 Hz.

Such displacements of the heart and therefore the lead system create geometry-controlled cyclic strains in the metallic wires that make up the conductive portion of the lead wire itself, accumulating up to 60 million cycles per year due to the heart rhythm alone.

In addition to chronic cyclic mechanical loading, cardiac lead wires 310, 312 may undergo some plastic deformation due to loads imparted to the system during implantation. Thus, lead wires 310, 312 will benefit from being capable of withstanding implant-load-related deformation and post-implant geometry-controlled cyclic deformation. Enhancement of lead wires 310, 312 may be realized by selection of metallic wire materials possessing high levels of fatigue endurance and ductility.

Advantageously, wires 310, 312 provide a high level of fatigue endurance strain in geometry-controlled loading and ductility and may therefore provide enhanced long term device performance when placed into any of a variety of cardiac lead designs. Also advantageously, wires 310, 312 are free of nickel, which may prevent adverse reaction in patients having a sensitivity to nickel (as also described below with regard to wire-based stents).

Wire made in accordance with the present process may also be used for leads for gastric, neurological, or other biological electrical stimulation.

3. Wire-Based Stents

Figure 11A:
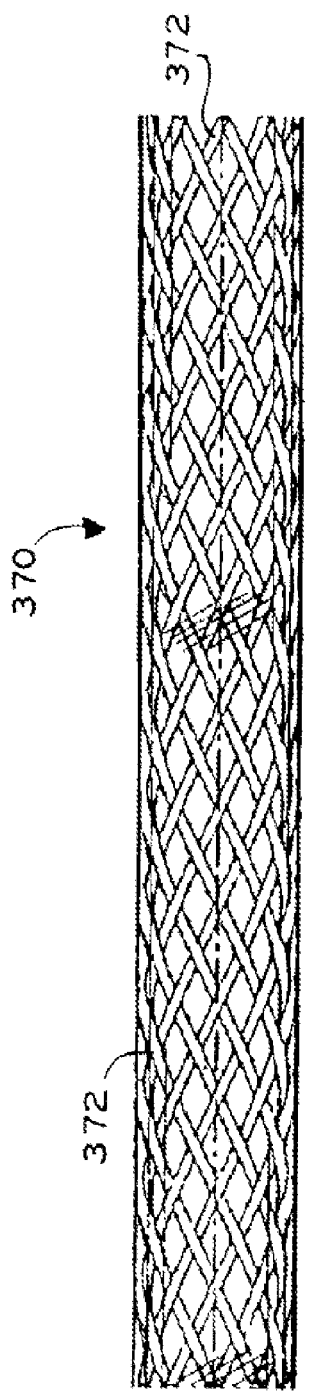
FIG. 11(a) is an elevation view of a braided tissue scaffold or stent including a wire made in accordance with the present process.
Figure 11B:
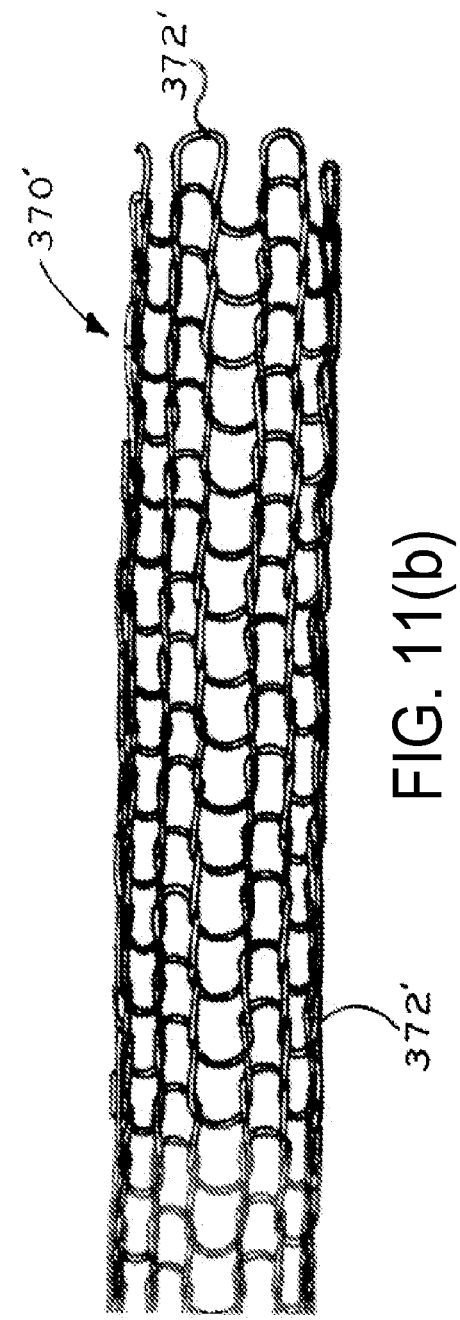
FIG. 11(b) is an elevation view of a knitted tissue scaffold or stent including a wire made in accordance with the present process.

Referring to FIG. 11(*a*), a tissue scaffold or vessel stent device 370 is shown which is made from one or more wires 372 made in accordance with the present process, which are braided, knitted, or otherwise formed together to produce the generally cylindrical cross-sectional shape of device 370.

Referring to and FIG. 11(*b*), a tissue scaffold or vessel stent device 370' is shown which is made from one or more wires 372' made in accordance with the present process, which are knitted together to form the generally cylindrical cross-sectional shape of device 370'.

Upon release from the delivery catheter, stents move to some degree, dependent on the relative vessel and device compliance, with the artery due to fluctuations in blood pressure, arterial vessel smooth muscle contraction and dilation, and due to general anatomical movement. Such mechanical displacement results in cyclic straining of wires 372, 372' comprising the structure of stent 370, 370' structure.

Non bioerodable tissue scaffolds or stents are generally implanted permanently, and therefore should be able to withstand millions of mechanical load cycles without losing structural integrity due to mechanical fatigue.

Stents 370, 370', which are constructed from wires 372, 372' made in accordance with the present process, possess a high degree of resistance to fatigue damage and thus offer optimized performance as compared to conventional stents made with wires having lower fatigue strength.

Advantageously, wire made in accordance with the present disclosure is also free of nickel, while preserving the shape-memory qualities and resistance to fatigue damage of wires containing nickel as a major constituent (e.g., NiTi). For patients sensitive to nickel, permanently implanted stents including nickel as part of the wire may not be a viable option. In such instances, wire made of the present Ti—Hf—Nb alloy may be a viable alternative with no loss in material performance.

While this disclosure has been described as having exemplary designs, the present disclosure can be further modified within the spirit and scope of this disclosure. This application is therefore intended to cover any variations, uses, or adaptations of the disclosure using its general principles. Further, this application is intended to cover such departures from the present disclosure as come within known or customary practice in the art to which this disclosure pertains and which fall within the limits of the appended claims.

What is claimed is:

1. A shape-memory wire for a medical device, the wire comprising:
   between 15 wt. % and 24.8 wt. % niobium;
   between 24 wt. % and 31 wt. % hafnium, zirconium, or a combination thereof;
   between 40 wt. % and 50 wt. % titanium; and
   between 0.4 wt. % and 0.6 wt. % chromium,
   the wire exhibiting superelastic behavior and having an austenitic finish temperature less than 37° C.

2. The shape-memory wire of claim 1, in combination with a medical device incorporating said shape-memory wire.

3. The combination of claim 2, wherein said medical device comprises one of a stent, a guidewire, an aneurysm occlusion device, a heart wall closure device, an orthodontic wire, and a surgical anchoring device.

4. The shape-memory wire of claim 1, wherein the wire comprises a drawn wire construct.

5. The shape-memory wire of claim 4, wherein the drawn wire construct comprises a round wire defining an outer diameter and an axial length.

6. The shape-memory wire of claim 1, wherein the wire has a diameter less than 10 mm.

7. The shape-memory wire of claim 1, wherein the wire comprises said niobium, said hafnium, zirconium, or a combination thereof and balance of said titanium.

8. The shape-memory wire of claim 1, wherein the wire has a modulus of elasticity between 50 GPa and 80 GPa.

9. The shape-memory wire of claim 1, wherein the wire exhibits a total isothermally recoverable strain of between 2% and 4% at 310K.

10. The shape-memory wire of claim 1, wherein the wire exhibits a fatigue life such that the wire survives $4 \times 10^6$ cycles at a strain amplitude of 0.8%.

11. The shape-memory wire of claim 1, wherein the wire exhibits a fatigue life such that the wire survives $2 \times 10^5$ cycles at a strain amplitude of 1.0%.

12. The shape-memory wire of claim 1, wherein the wire exhibits a fatigue life such that the wire survives $10^4$ cycles at a strain amplitude of 1.2%.

13. The shape-memory wire of claim 1, wherein the wire comprises a flat material.

14. The shape-memory wire of claim 1, wherein the wire comprises a hollow tube material.

15. The shape-memory wire of claim 1, wherein the wire comprises a rod material having a diameter of less than 5 mm.

16. The shape-memory wire of claim 1, wherein the wire comprises a continuous wire wound onto a spool.

17. The shape-memory wire of claim 1, wherein the wire does not include nickel as an alloy constituent.

18. The shape-memory wire of claim 1, wherein the wire is nickel-free.

19. A method for producing a shape-memory wire for a medical device, the method comprising:
   imparting between 50% and 99% cold work to a wire including:
   between 40 wt. % and 50 wt. % titanium,
   between 15 wt. % and 24.8 wt. % niobium,
   between 24 wt. % and 31 wt. % hafnium, zirconium or a combination thereof, and
   between 0.4 wt. % and 0.6 wt. % chromium, such that a resulting cold worked wire construct has a final diameter of less than 10 mm; and
   shape-setting the cold-worked wire construct by annealing the cold worked wire construct at a time and temperature sufficient to restore a majority of the wire material to the parent material phase, the shape-setting step performed while a stress is applied to the wire construct, the cold-worked wire construct exhibiting superelastic behavior and having an austenitic finish temperature less than 37° C.

20. The method of claim 19, further comprising, after the step of shape-setting, incorporating the shape-set wire construct into the medical device.

21. The method of claim 20, wherein the medical device is one of a stent, a guidewire, an aneurysm occlusion device, a heart wall closure device, an orthodontic wire, and a surgical anchoring device.

22. The method of claim 19, wherein the stress applied to the wire construct is a tension force sufficient to hold the wire in a substantially linear configuration.

23. The method of claim 19, wherein the stress applied to the wire construct is a constraint of the wire construct in a specific non-linear shape to effect a final desired geometry.

* * * * *